US011085936B2

(12) United States Patent
Wan et al.

(10) Patent No.: US 11,085,936 B2
(45) Date of Patent: Aug. 10, 2021

(54) METHOD AND A KIT FOR SIMULTANEOUS ANALYSES OF THYROID HORMONES AND RELATED METABOLITES IN SERUM

(71) Applicant: Peking University, Beijing (CN)

(72) Inventors: Yi Wan, Beijing (CN); Hongyang Cui, Beijing (CN); Hang Liu, Beijing (CN); Shixiong Gao, Beijing (CN)

(73) Assignee: Peking University, Beijing (CN)

( * ) Notice: Subject to any disclaimer, the term of this patent is extended or adjusted under 35 U.S.C. 154(b) by 348 days.

(21) Appl. No.: 16/378,802

(22) Filed: Apr. 9, 2019

(65) Prior Publication Data

US 2020/0326352 A1 Oct. 15, 2020

(51) Int. Cl.
*G01N 33/78* (2006.01)
*G01N 1/40* (2006.01)

(52) U.S. Cl.
CPC .......... *G01N 33/78* (2013.01); *G01N 1/4055* (2013.01); *G01N 1/4077* (2013.01); *G01N 2001/4061* (2013.01); *G01N 2001/4088* (2013.01)

(58) Field of Classification Search
CPC .... G01N 21/76; G01N 33/582; G01N 33/587; G01N 21/05; G01N 33/725; G01N 2021/0346; B01L 3/5027; B01L 2300/0663; B01L 2300/0877; B01L 2300/0883; B01L 2300/123
See application file for complete search history.

(56) References Cited

U.S. PATENT DOCUMENTS

2013/0140449 A1* 6/2013 Banks ................ G01N 33/6848 250/282

* cited by examiner

Primary Examiner — Jennifer Wecker
Assistant Examiner — Michael Paul Shimek
(74) Attorney, Agent, or Firm — SV Patent Service

(57) ABSTRACT

A method and kit the simultaneous analysis of thyroid hormones (THs) and related metabolites in serum are disclosed. The method includes the extraction of THs and related metabolites, the derivatization of THs and related metabolites with 5-N-succinimidoxy-5-oxopentyl)triphenylphosphonium bromide (SPTPP), and the analysis of SPTPP derivatives using ultra-high-performance liquid chromatography-tandem mass spectrometry (UPLC-MS/MS). Free or total THs (T3 and T4) together with their related metabolites (MIT, DIT, T0, T1, rT1, 3,3'-T2, 3,5-T2, and rT3) can be determined simultaneously, rapidly, and accurately. This invention overcomes the limitation that the traditional method can only be used for the analysis of T3 and T4 with low specificity. The invention exhibits extremely high analytical sensitivity for all of the target analytes (femtogram level). Moreover, this invention also possesses numerous other advantages, such as simple sample pretreatment, accurate determination, low cost, high efficiency, effective separation, and small sample amounts.

18 Claims, 10 Drawing Sheets

METHOD AND A KIT FOR SIMULTANEOUS ANALYSES OF THYROID HORMONES AND RELATED METABOLITES IN SERUM

FIELD OF THE INVENTION

This invention belongs to the field of biochemical analysis, and in particular, to methods and kits for the simultaneous analysis of thyroid hormones and related metabolites.

BACKGROUND OF THE INVENTION

Thyroid hormones (THs) secreted by the thyroid play important roles in the growth, development, and metabolism of humans and animals. At present, the traditional chemiluminescence (CL) method can only detect free and total T3 and T4 in serum. However, the specificity and sensitivity of the CL method are not high. Furthermore, some studies have indicated that TH-related metabolites (e.g., T2) also play important roles in various functions; for example, see *American Journal of Physiology-Endocrinology and Metabolism*, 296(3), E497-E502. Some researchers have developed a liquid chromatography-mass spectrometry (LC-MS/MS) method for the analysis of five THs (3,3'-T2, 3,5-T2, T3, rT3, and T4) in serum samples; for example, see *Analytical and Bioanalytical Chemistry*, 397, 1831-1839. However, owing to the high detection limits of this method, only total T3 and T4 could be detected. Moreover, this method suffers from several limitations, such as low sensitivity, strong matrix effects, complex sample preparation procedures, and large sample amount.

SUMMARY OF THE INVENTION

In one aspect, the present invention provides a method and kit for simultaneous analysis of THs and related metabolites in serum. This method includes the extraction of THs and related metabolites, the derivatization of THs and related metabolites with (5-N-succinimidoxy-5-oxopentyl) triphenylphosphonium bromide (SPTPP), and the analysis of SPTPP derivatives using ultra-high-performance liquid chromatography-tandem mass spectrometry (UPLC-MS/MS). With this invention, free THs and related metabolites can be simultaneously and accurately determined using only 200 μL of serum, and total THs and related metabolites can also be simultaneously and accurately determined using only 10 μL of serum. The disclosed methods and kits overcome the instability, lack of specificity, and low sensitivity of the traditional method. The disclosed methods and kits possess numerous advantages, such as high reproducibility, high specificity, high sensitivity, simplified sample pretreatment, small sample amount, and simultaneous analysis of free or total THs and related metabolites.

The implementation of the present invention can include the following:

In one aspect, the present invention provides a method and a kit for simultaneous analysis of THs and related metabolites in serum. This method includes the extraction of THs and related metabolites, the derivatization of THs and related metabolites with SPTPP, and the analysis of SPTPP derivatives using UPLC-MS/MS. Based on the above methods, so that THs and related metabolites can be simultaneously and accurately determined.

It should be noted that the THs and related metabolites mentioned above include free THs and related metabolites and total THs and related metabolites.

It should be further noted that the THs and related metabolites mentioned above include MIT, DIT, T0, T1, rT1, 3,3'-T2, 3,5-T2, T3, rT3, and T4.

In some embodiments, the free THs and related metabolites are the non-protein-bound compounds. These can be obtained by centrifugation using Centrifree YM-30 ultrafiltration devices (30 kDa molecular weight cutoff, Millipore, Bedford, Mass.).

Further, in the extraction method for free THs and related metabolites, a 200-500 μL sample of human serum is filtered through a Centrifree YM-30 ultrafiltration device (30 kDa molecular weight cutoff, Millipore, Bedford, Mass.) with centrifugation at 37° C. for 30 min. Then, 100 μL of the ultrafiltrate is collected and spiked with 50 μL of internal standard (IS) working solution.

Further, the centrifugal force used with the Centrifree YM-30 ultrafiltration devices can be 1,000-2,000×g. The IS working solution contains a mixture of $^{13}C_6$-MIT, $^{13}C_6$-3,3'-T2, $^{13}C_6$-T3, and $^{13}C_6$-T4 (100 ng/L for each compound) and citric acid, L-ascorbic acid, and DL-dithiothreitol (50 g/L for each compound) dissolved in methanol.

In some embodiments, the total THs and related metabolites are the sum of the protein-bound and non-protein-bound target compounds. Deproteination can be performed to release the protein-bound THs and related metabolites in the serum and obtain the total concentrations of the target compounds.

Further, in the extraction method for total THs and related metabolites, a 10-50 μL sample of human serum spiked with 50 μL of freshly prepared IS working solution is added to a glass centrifuge tube. The solution mixture is maintained below 0° C. for 15 min to ensure the release of protein-bound THs. Then, the sample is centrifuged at 3,500×g for 5-20 min. The supernatant is collected in a new glass vial and the precipitate in the tube is extracted twice with 45 μL of methanol. Then, the supernatant and extracts are combined.

In some embodiments, the SPTPP derivatization procedure includes the following steps: 30 μL of derivatization buffer and 20 μL of derivatization reagent are added to the extracts of free or total THs and related metabolites; after vortex mixing, the mixed solution is heated at 40° C. for 20 min; and 600 μL of a termination solution is added to the reaction mixture.

In some embodiments, the derivatization buffer is 0.1 M pH 8.0 phosphate-buffered saline (PBS). The derivatization reagent is SPTPP dissolved in DMSO to a concentration of 30 mM. The termination solution is 1 M NaOH solution.

In all embodiments, the invention also includes the steps of purification, extraction, and concentration prior to UPLC-MS/MS analysis. Specifically, ethyl acetate is used to purify the reaction mixture after the addition of the termination solution. After purification, an acidifier is added to the purified reaction mixture. Then, ethyl acetate is used to extract the SPTPP derivatives from the purified reaction mixture. Next, the extracts are dried with nitrogen and redissolved in methanol for UPLC-MS/MS analysis.

Preferably, 800 μL of ethyl acetate is used to purify the reaction mixture one to three times. The acidifier is 5 M HCl solution. The acidified purified reaction mixture is extracted twice with 800 μL of ethyl acetate, and the extracts are transferred to a new 2 mL glass vial. All of the purification and extraction steps are performed over ice. Next, the extracts are dried with nitrogen and redissolved in 50 μL of methanol. Finally, the samples are transferred into glass vials for UPLC-MS/MS analysis.

In some embodiments, the specific steps of UPLC-MS/MS analysis can include the follows: calibration standards of THs and related metabolites are prepared in water as dilution series; calibration standards and serum samples are derivatized with SPTPP; all of the samples are analyzed using UPLC-MS/MS; calibration curves are constructed by plotting the area ratio of each analyte relative to its IS versus the respective analyte concentrations, and these data are fitted using linear regression; and the amount of each TH and related metabolite in a serum sample is then interpolated using this linear function.

In some embodiments, the standard solutions of THs and related metabolites are prepared to obtain associated calibration curves using the following methods:

(1) The standard stock solutions of THs and related metabolites are prepared individually at a concentration of 100 μg/mL in methanol containing 0.1 M ammonium hydroxide. The solutions are stored away from light at −80° C.

(2) The working standard solution is prepared by mixing and diluting each standard stock solution to a concentration of 1 μg/mL in methanol.

(3) Calibration curves for free THs and related metabolites are prepared by diluting the working standard solution to concentrations of 0.25 ng/L, 1.00 ng/L, 5.00 ng/L, 20 ng/L, 50 ng/L, and 150 ng/L in water and derivatizing the calibration samples with SPTPP.

(4) Calibration curves for total THs and related metabolites are prepared by diluting the working standard solution to concentrations of 0.01 ng/mL, 0.1 ng/mL, 0.5 ng/mL, 2.5 ng/mL, 5 ng/mL, 25 ng/mL, and 150 ng/mL in water and derivatizing the calibration samples with SPTPP.

In some embodiments, the parameters used for UPLC-MS/MS analysis are as follows: UPLC is performed on a Poroshell 120 HPH-C18 column (2.1×100 mm, 2.7 μm, Agilent). The column and sampler temperatures are maintained at 40° C. and 4° C., respectively. The mobile phase, operating at a flow rate of 0.3 mL/min, consists of methanol as solvent A and Milli-Q water as solvent B. A total of 2-10 μL of each sample is injected onto the column. The gradient elution starts at 30% A and is held for 1 min and then increased to 60% A at 15 min, 75% A at 17 min, and 100% A at 18 min. After washing with 100% A for 8 min, the column is re-equilibrated with 30% A for 4 min prior to the next injection. The mass spectrometer is operated in the positive electrospray ionization (ESI) mode with multiple reaction monitoring (MRM). The conditions for ESI-MS/MS detection are optimized to obtain the highest signal intensity and are as follows: capillary voltage: 3-3.2 kV; desolvation temperature: 500° C.; source temperature: 150° C.; desolvation gas flow rate: 1000 L/h; cone gas flow rate: 150 L/h.

The present invention also provides a kit for the determination of THs and related metabolites in serum. The kit includes the standard stock solution, extraction reagents, and IS working solution containing a mixture of $^{13}C_6$-MIT, $^{13}C_6$-3,3'-T2, $^{13}C_6$-T3, and $^{13}C_6$-T4 (100 ng/L for each compound) and citric acid, L-ascorbic acid, and DL-dithiothreitol (50 g/L for each compound) dissolved in methanol.

Moreover, the kit also includes the materials for SPTPP derivatization. The derivatization materials include the derivatization buffer, derivatization reagent, termination solution, and acidifier. The derivatization buffer is 0.1 M PBS (pH 8.0). The derivatization reagent is SPTPP dissolved in DMSO to a concentration of 30 mM. The termination solution is 1 M NaOH solution. The acidifier is 5 M HCl solution.

The disclosed methods and kits can include one or more of the following advantages:

(1) This invention can be used to accurately determine the concentrations of free and total THs and related metabolites in serum. The ionization efficiency of SPTPP derivatives is significantly higher than that for underivatized compounds. Thus, the analytical sensitivity can be greatly improved. Therefore, this invention permits the accurate and rapid determination of free and total THs and related metabolites using only a small amount of serum. In addition to thyroid hormones T3 and T4, the levels of TH-related metabolites (MIT, DIT, T0, T1, rT1, 3,3'-T2, 3,5-T2, and rT3) can also be simultaneously determined.

(2) This invention also possesses additional advantages, such as high reproducibility, high specificity, high sensitivity, simple sample pretreatment, convenient operation, and low sample amounts.

(3) Liquid-liquid extraction is used for the purification of the reaction mixture. This simple purification method can greatly reduce the influence of the complex matrix components present in the derivatization mixture and also decrease the cost of pretreatment.

(4) To ensure the accuracy of the quantitative analyses, carbon-13-labeled THs and related metabolites are used as ISs in this invention. On the basis of the similarity of structures and retention times (RT), $^{13}C_6$-MIT is used as the IS for MIT, DIT, and T0; $^{13}C_6$-3,3'-T2 is used as the IS for T1, rT1, 3,3'-T2, and 3,5-T2; $^{13}C_6$-T3 is used as the IS for T3 and rT3; and $^{13}C_6$-T4 is used as the IS for T4.

(5) UPLC-MS/MS is used to analyze the SPTPP derivatives. The use of this technique provides high efficiency, simple sample preparation, good separation of analytes, and lower cost, and is highly recommended.

(6) Compared with traditional methods, this invention requires only a small sample amount and simple pretreatment and provides accurate determination and strong analytical specificity. Moreover, SPTPP derivatives are very stable and the quantitative analysis results remain unchanged for at least five days. The SPTPP derivatives can be stored stably at −20° C. for at least two months.

(7) The concentrations of free and total T3 and T4 determined using this invention were compared to those obtained via the traditional CL method. A strong correlation was observed for the results obtained using the two methods. This indicates that this invention can replace the traditional CL method for THs analysis. Furthermore, this invention overcomes the limitation that the traditional CL method cannot be used to analyze TH metabolites including MIT, DIT, T0, T1, rT1, 3,3'-T2, 3,5-T2, and rT3.

(8) This invention is suitable for the analysis of a wide range of analyte concentrations. In addition, the limit of detection can be extremely low.

DETAILED DESCRIPTION OF IMPLEMENTATIONS

Figure 1:
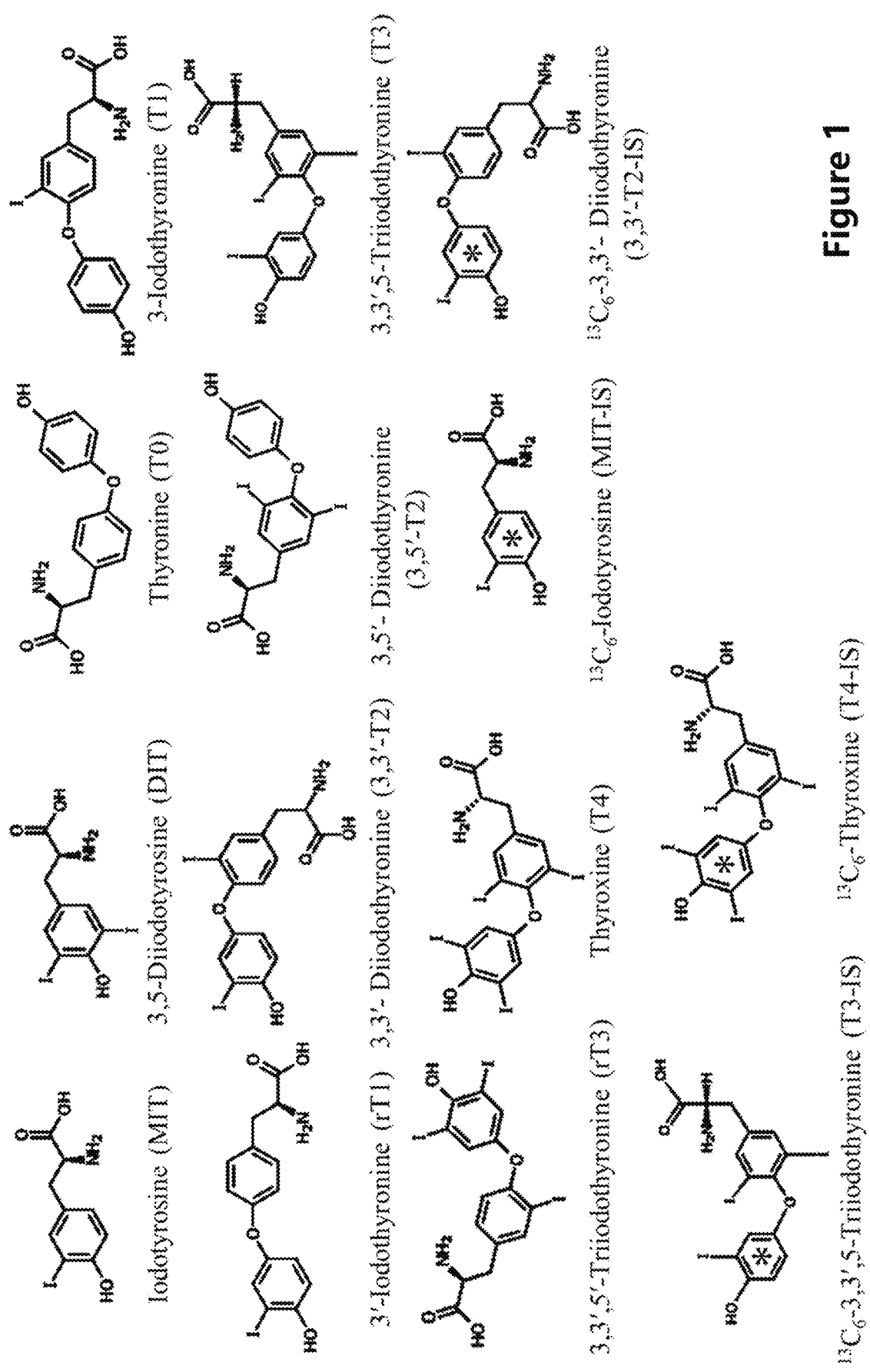
FIG. 1 shows the molecular structures of THs and related metabolites and the four $^{13}C_6$ analogues used as ISs.
Figure 2:
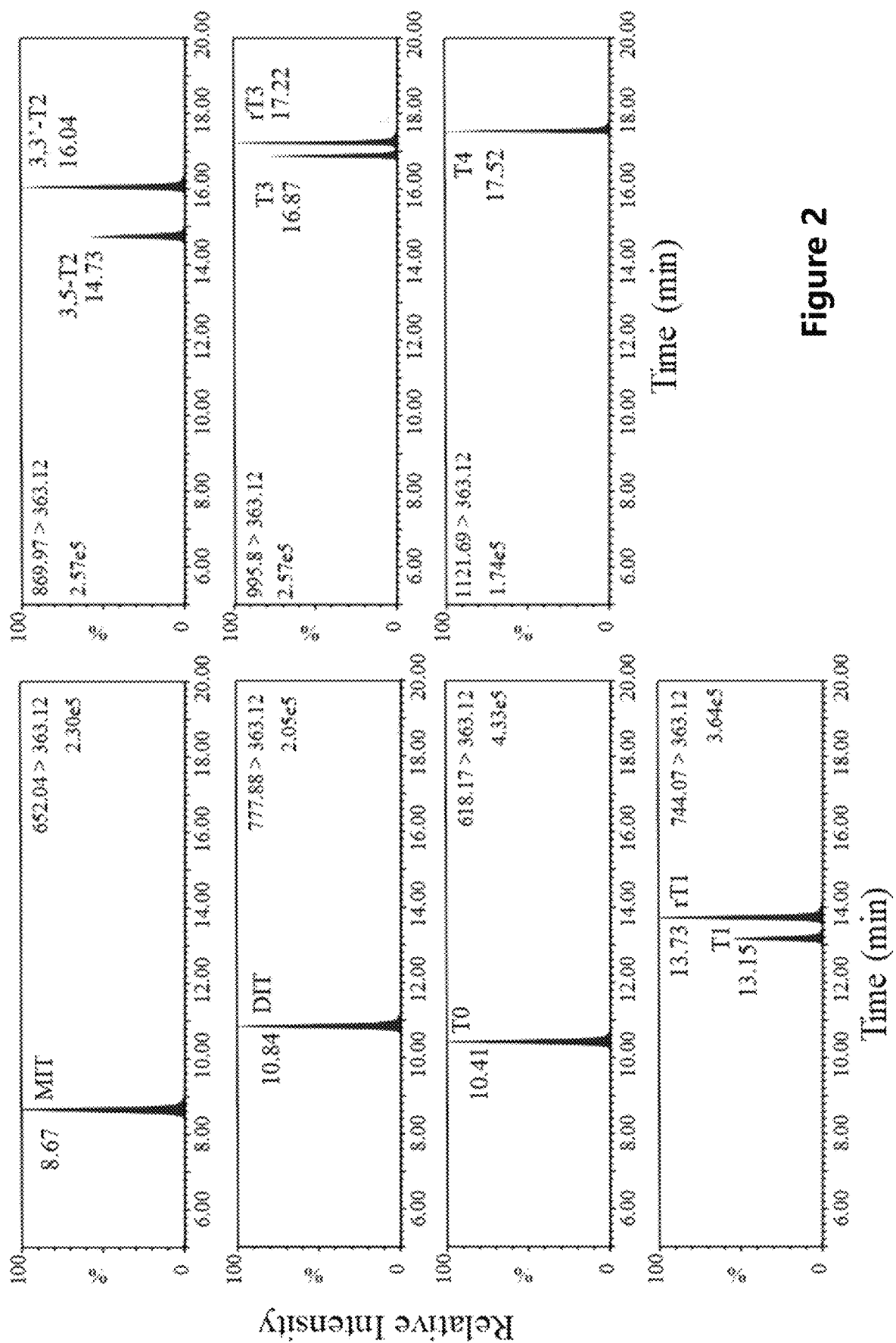
FIG. 2 shows UPLC-MS/MS MRM chromatographic profiles of the SPTPP-derivatized target analytical standards in a human serum sample that was spiked with THs and related metabolites.
Figure 3:
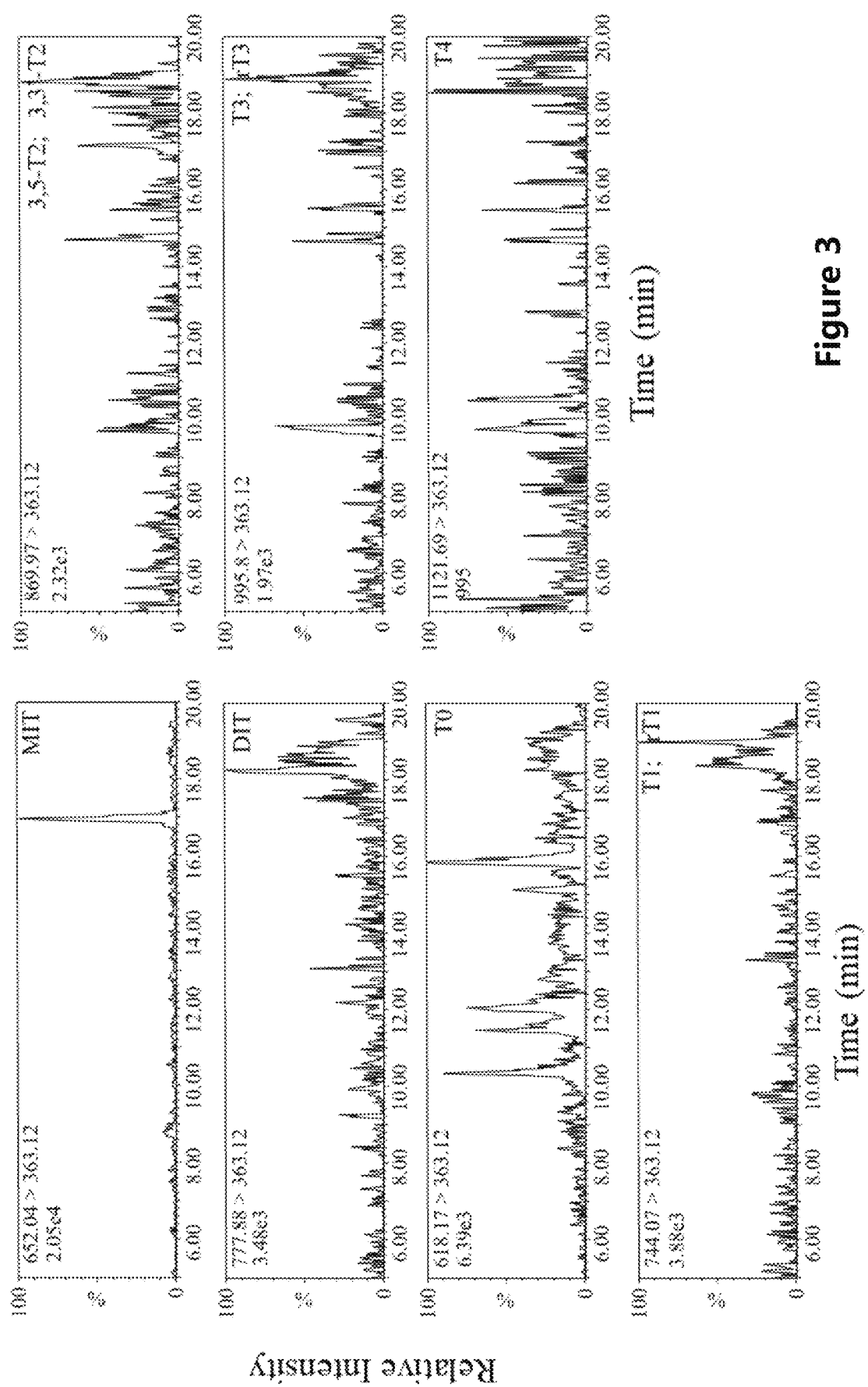
FIG. 3 shows UPLC-MS/MS MRM chromatographic profiles of a SPTPP-derivatized control sample without any THs or related metabolites.
Figure 4:
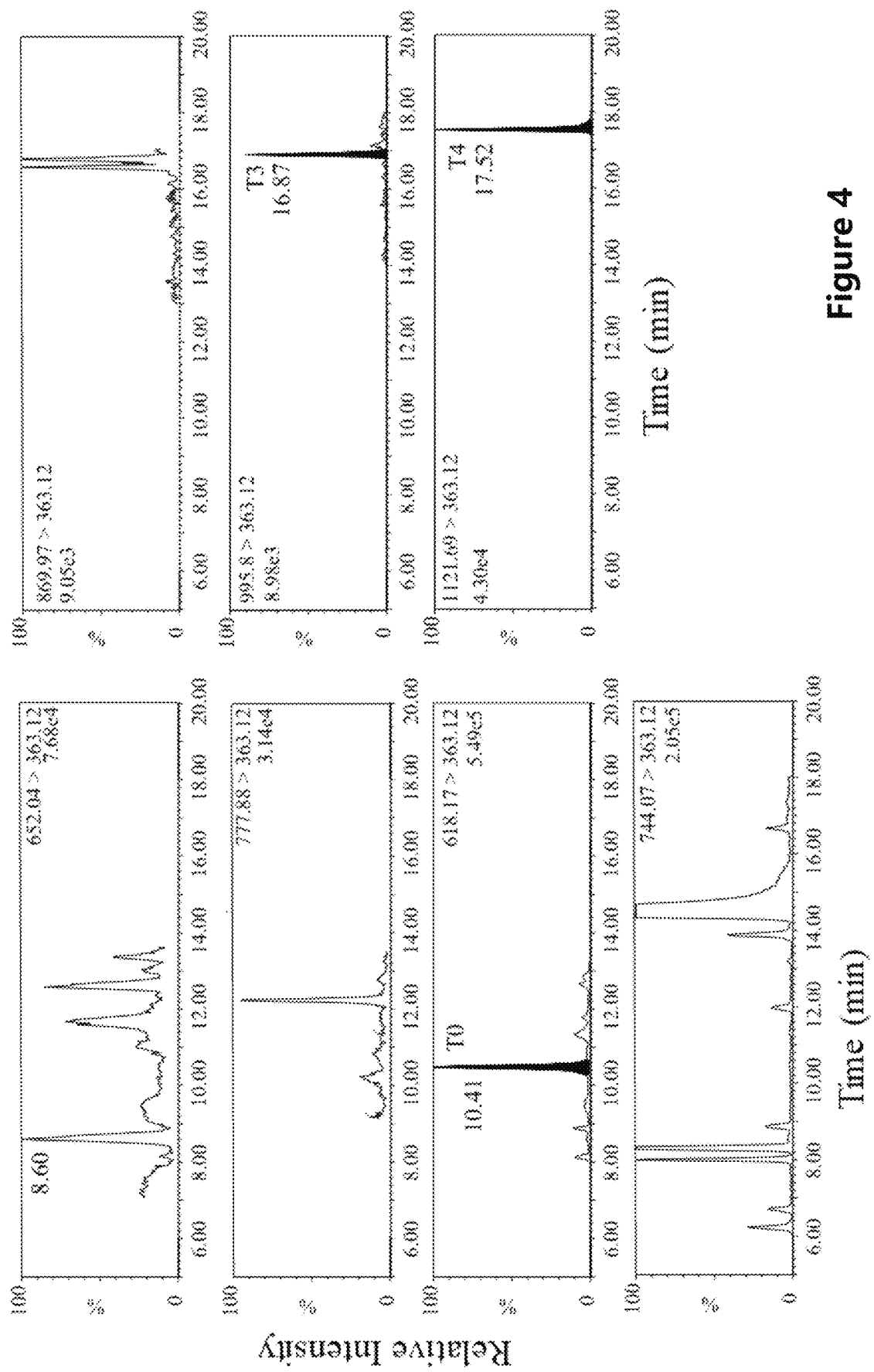
FIG. 4 shows UPLC-MS/MS MRM chromatographic profiles of SPTPP-derivatized free THs and related metabolites in a serum sample.
Figure 5:
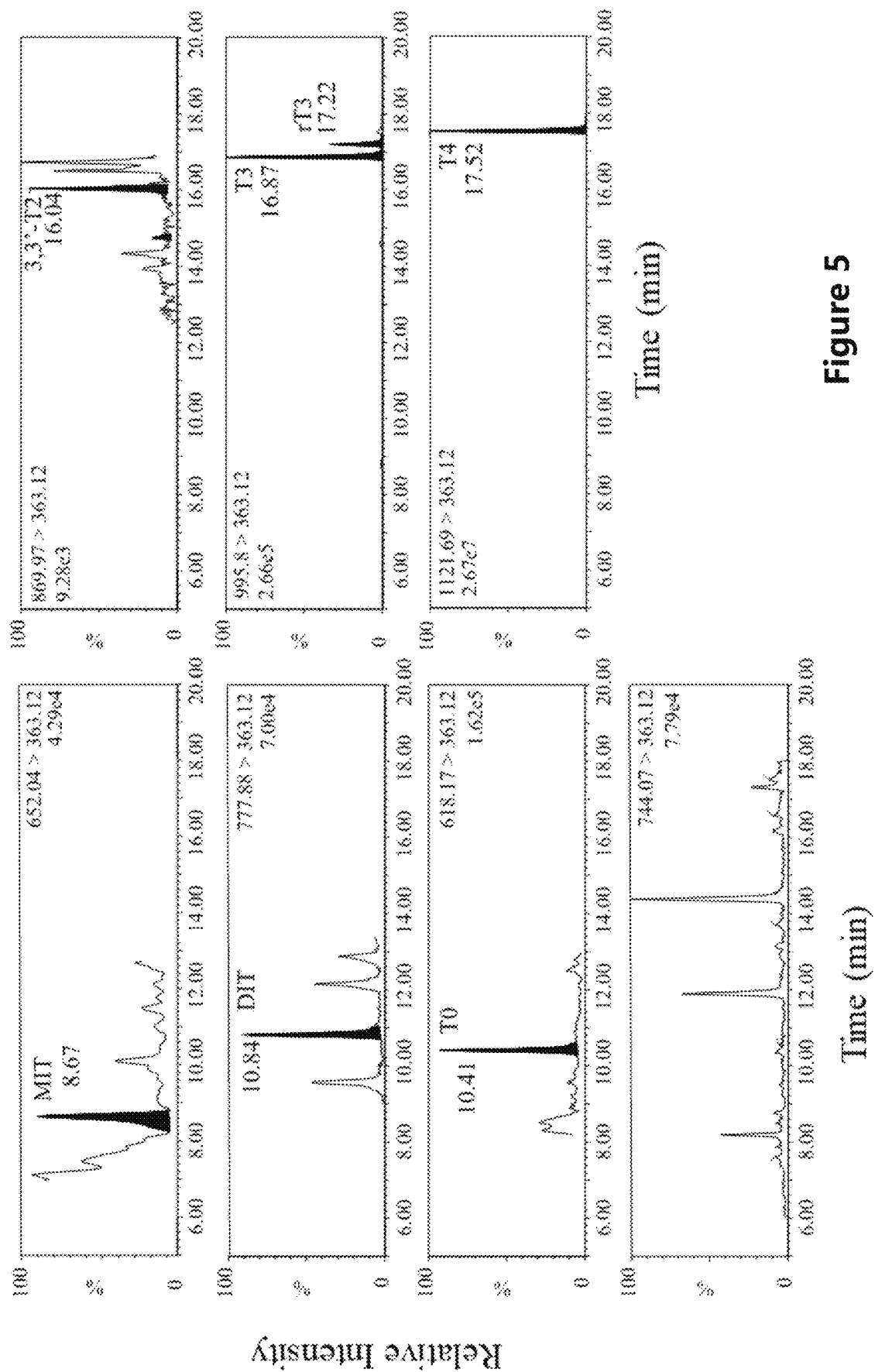
FIG. 5 shows UPLC-MS/MS MRM chromatographic profiles of a SPTPP-derivatized total THs and related metabolites in a serum sample.
Figure 6:
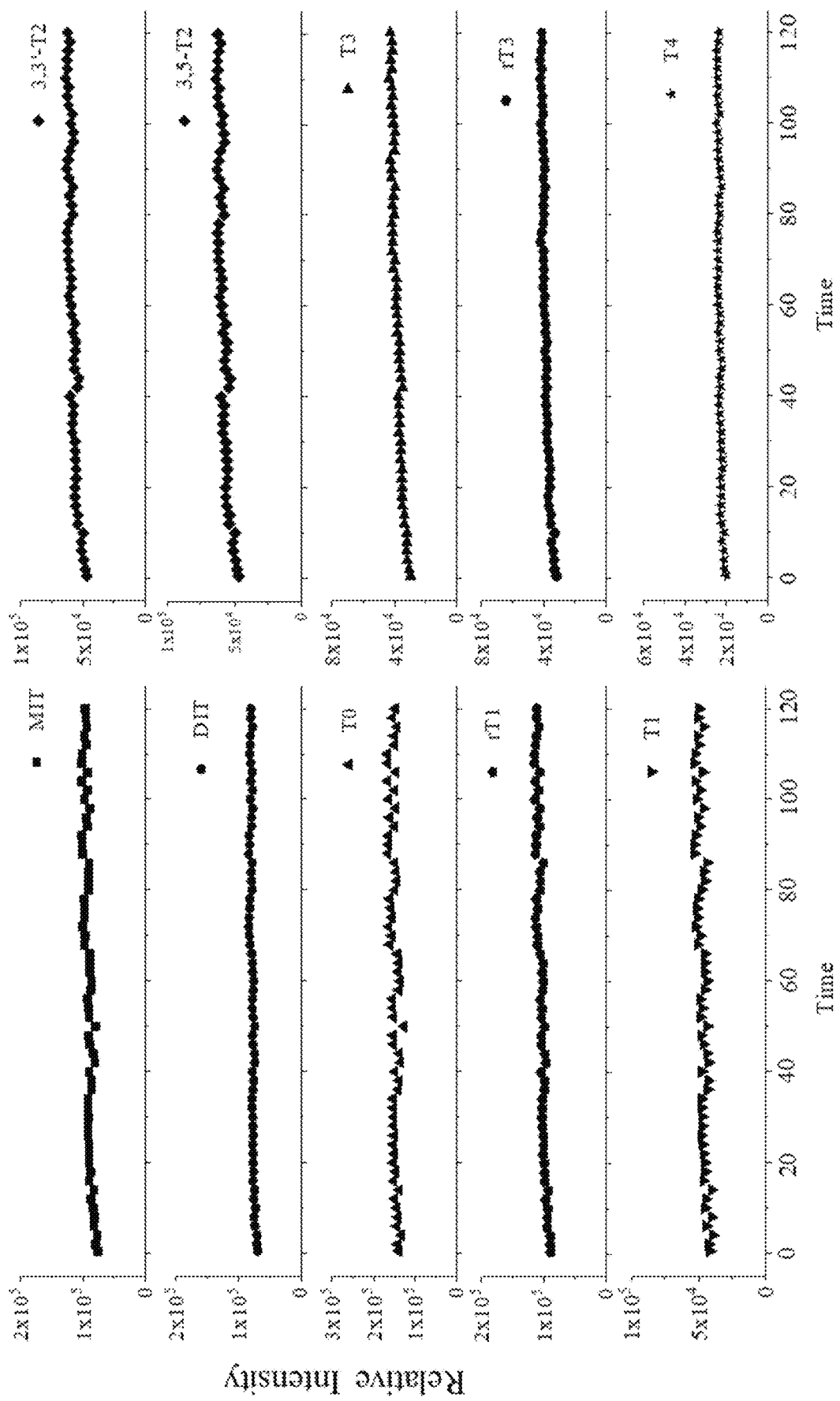
FIG. 6 shows the stability of the SPTPP derivatives.
Figure 7:
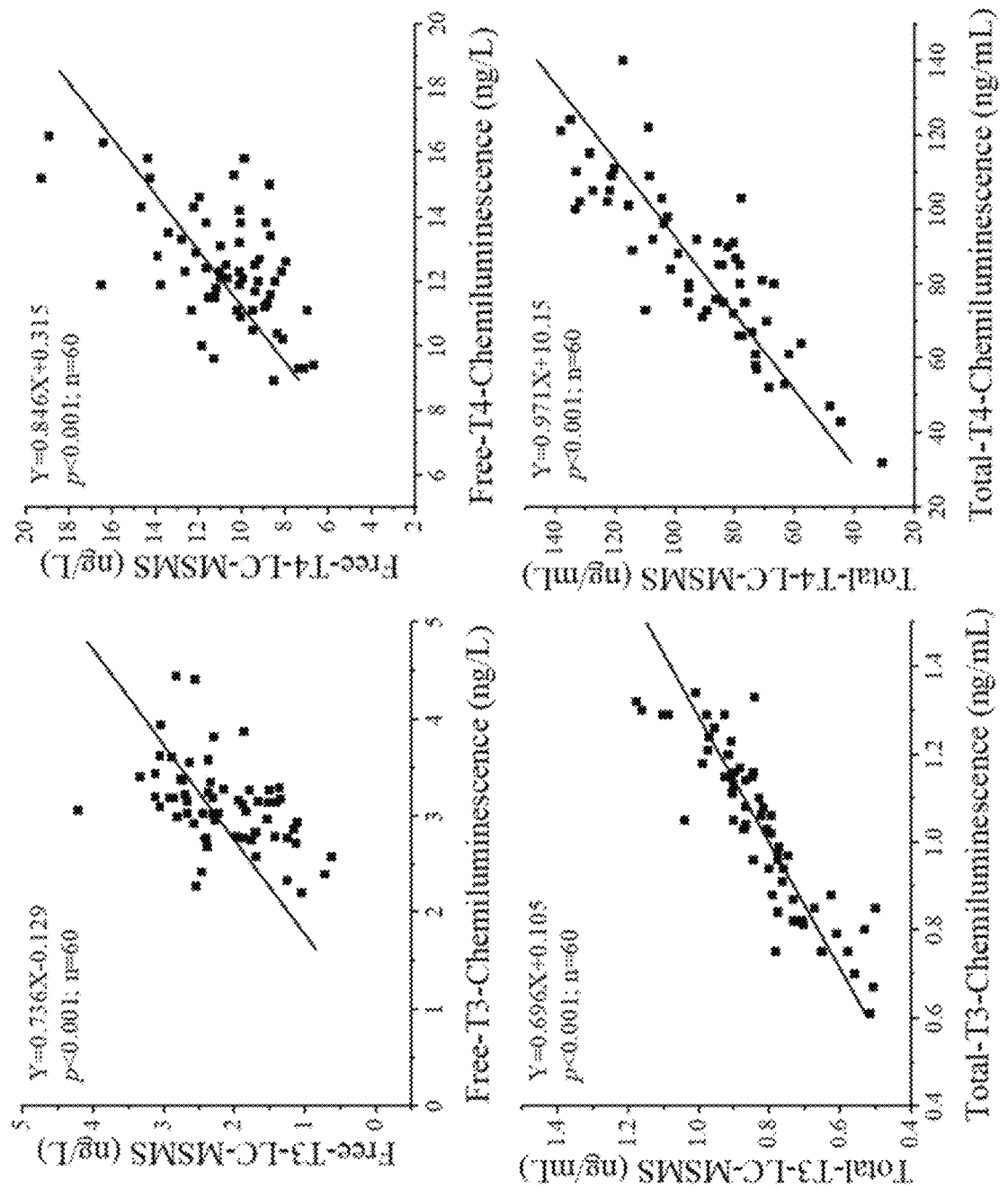
FIG. 7 shows a comparison between the CL method and the UPLC-MS/MS method (this invention).
Figure 8:
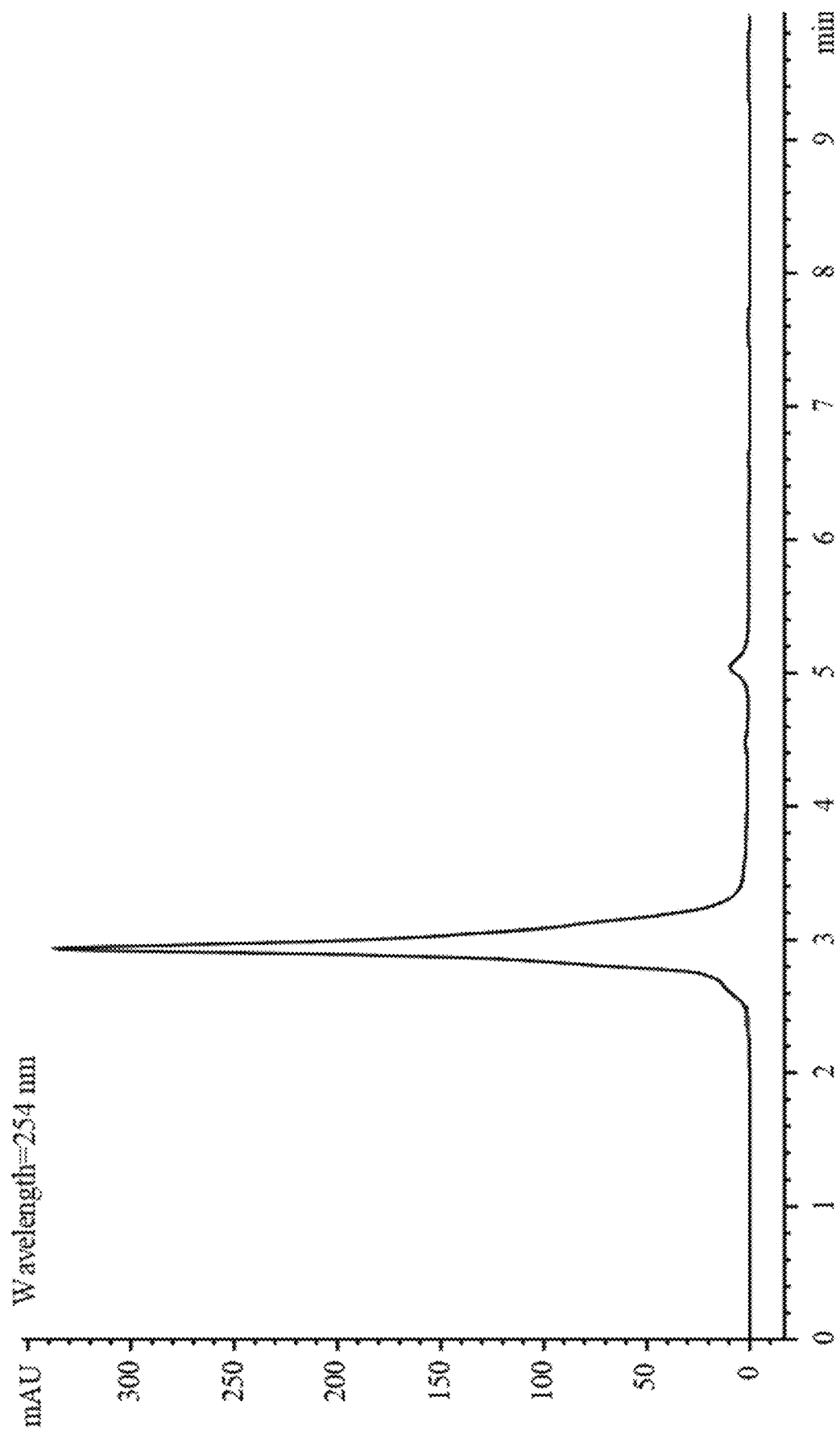
FIG. 8 shows a liquid chromatogram of SPTPP.
Figure 9:
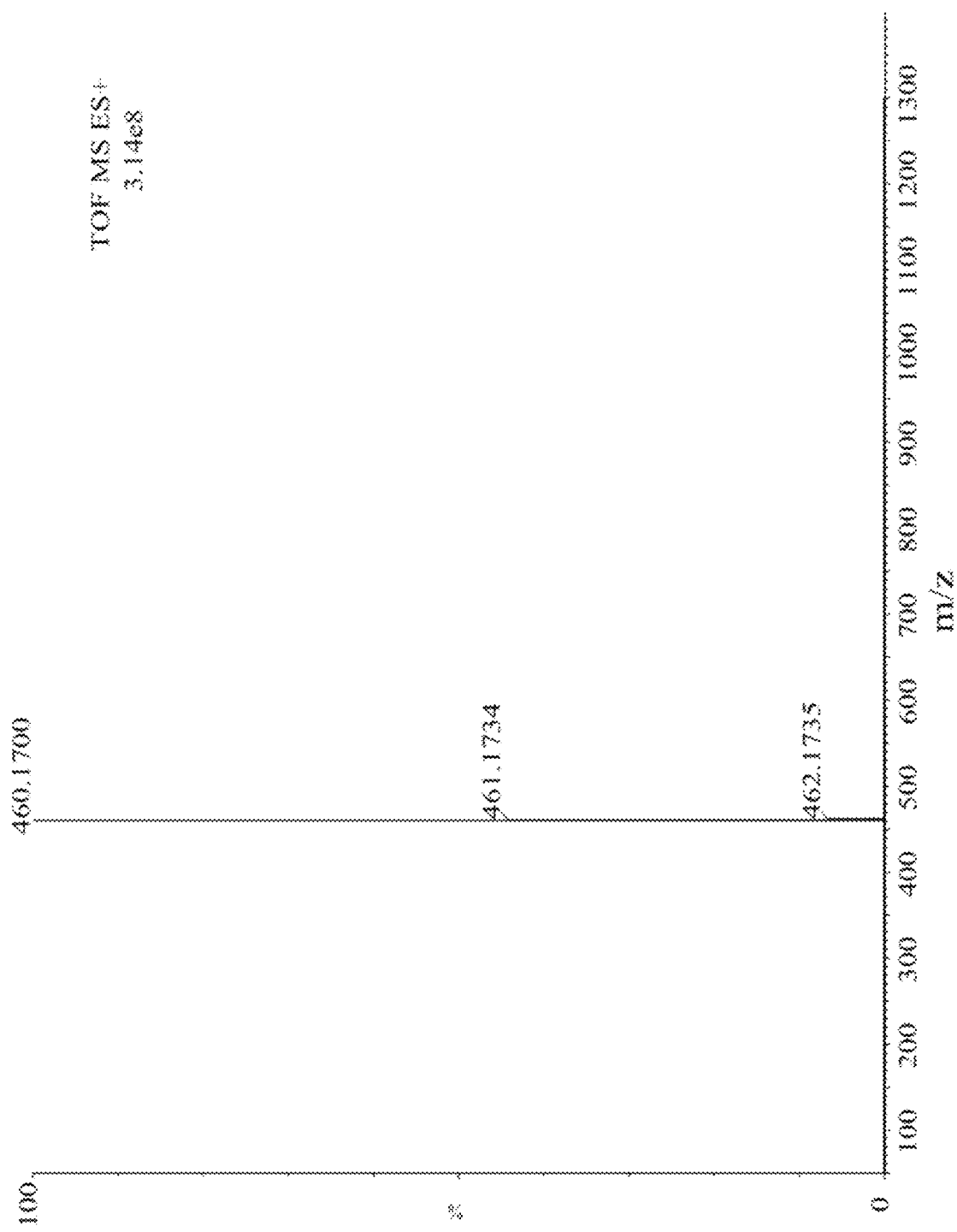
FIG. 9 shows a time-of-flight mass spectrum of SPTPP.
Figure 10:
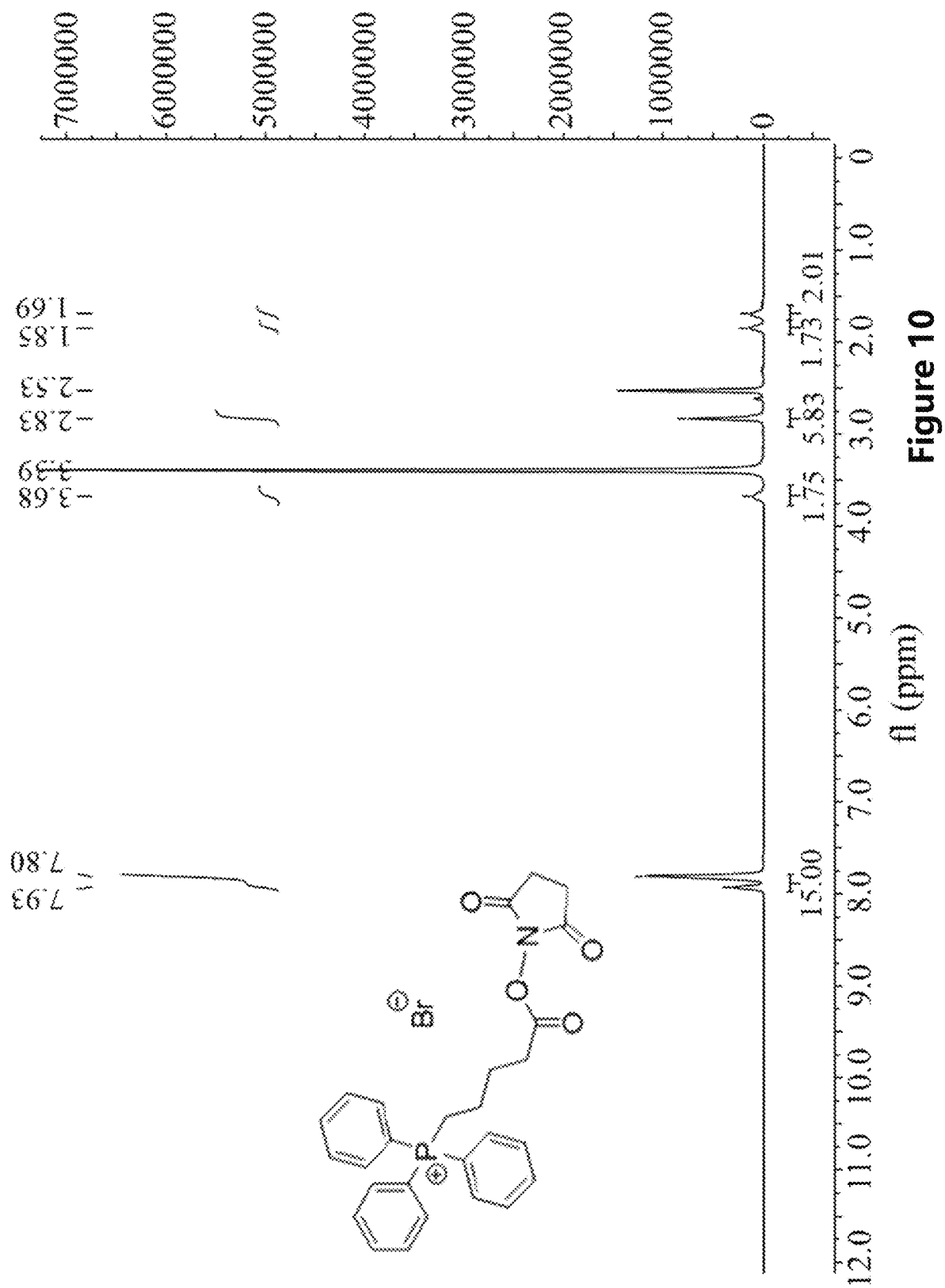
FIG. 10 shows a $^1$H NMR spectrum of SPTPP.

This invention provides an analytical method for THs and related metabolites. Any sample containing or suspected of containing THs and related metabolites can be used, such as samples of serum, blood, urine, or sewage. The samples may contain both free and protein-bound THs and related metabolites.

Extraction of Free or Total THs and Related Metabolites

The sample is filtered through a Centrifree YM-30 ultrafiltration device (30 kDa molecular weight cutoff, Millipore, Bedford, Mass.) to afford an ultrafiltrate containing free THs and related metabolites. The sample should be deproteinated for extraction of the total THs and related metabolites. This can be achieved by adding methanol with the ISs, followed by vortexing and centrifugation.

Sample Preparation

The extracts of free or total THs and related metabolites are subsequently derivatized with SPTPP. The derivatives are further purified using liquid-liquid extraction and then concentrated prior to UPLC-MS/MS analysis.

UPLC Separation of SPTPP Derivatives

The SPTPP-derivatized THs and related metabolites are separated using UPLC methods known to those skilled in the art. For example, the SPTPP derivatives can be separated using UPLC with a Poroshell 120 HPH-C18 column or a BEH Phenyl column.

Tandem Mass Spectrometry Analysis

The SPTPP derivatives are analyzed using a triple-quadrupole mass spectrometer operating in the positive ESI mode. The SPTPP-derivatized THs and related metabolites are identified on the basis of their retention times and ratios of molecular ions and fragment ions. To ensure the accuracy of the quantitative analyses, carbon-13-labeled THs and related metabolites are used as ISs in this invention. On the basis of the similarity of structures and retention times, $^{13}C_6$-MIT is used as the IS for MIT, DIT, and T0; $^{13}C_6$-3,3'-T2 is used as the IS for T1, rT1, 3,3'-T2, and 3,5-T2; $^{13}C_6$-T3 is used as the IS for T3 and rT3; and $^{13}C_6$-T4 is used as the IS for T4. Calibration curves for known concentrations of the SPTPP-derivatized THs and related metabolites are measured for quantitation.

IMPLEMENTATION EXAMPLES

The following examples present the analytical methods for free and total THs and related metabolites in more detail. The invention will be demonstrated by the following examples, which are provided to demonstrate but not limit the embodiments of the present invention.

Example 1. Analysis of Free THs and Related Metabolites in Serum

1. Instruments and Reagents

ACQUITY Ultra Performance LC system (Waters, Milford, Mass., USA). Waters Xevo TQ-XS Triple Quadrupole Mass Spectrometer equipped with an ESI source (Waters, USA). Refrigerated centrifuge (Hermle Labortechnik, Wehingen, Germany). Analytical balance (Mettler, USA). N☐EVAP analytical evaporator (Berlin, Mass., USA). Vortex mixer (Vortex-Genie 2).

Methanol and ethyl acetate (LC/MS grade) were obtained from Merck (Darmstadt, Germany). DMSO (HPLC grade) was purchased from Shanghai Aladdin Industrial Corporation. Ultrapure water was acquired from a Milli-Q water purification system (Millipore Corporation, Hayward, Calif., USA) operating at 18.2 MΩ·cm. Sodium hydroxide (NaOH, Guaranteed Reagent) and hydrochloric acid (HCl, Guaranteed Reagent) were purchased from Xilong Scientific Co., Ltd. (Chengdu, China). Citric acid, L-ascorbic acid, and DL-dithiothreitol (purities above 99%) were obtained from Acros Organics. SPTPP was synthesized based on the method described in Rapid Communications in Mass Spectrometry, 2010, 24, 1358-1364.

MIT (purity >95%), DIT (purity >95%), T0 (purity >98%), T1 (purity >95%), rT1 (purity >95%), 3,5-T2 (purity >99%), rT3 (purity >95%), T4 (purity >95%), $^{13}C_6$-MIT (purity >98%), $^{13}C_6$-T3 (purity >98%), and $^{13}C_6$-T4 (purity >98%) were obtained from Toronto Research Chemicals (Downsview, ON, Canada). 3,3'-T2 (purity >98%) and $^{13}C_6$-3,3'-T2 (purity >98%) were purchased from USBiological (Swampscott, Mass., USA). T3 (purity >97%) was obtained from Sigma Aldrich (Oakville, ON, Canada).

The standard stock solutions of THs and related metabolites were prepared individually at a concentration of 100 μg/mL in methanol containing 0.1 M ammonium hydroxide and stored in the dark at −80° C.

The working standard solution was prepared by mixing and diluting the standard stock solutions to a concentration of 1 μg/mL for each compound.

The IS stock solutions of $^{13}C_6$-MIT, $^{13}C_6$-3,3'-T2, $^{13}C_6$-T3, and $^{13}C_6$-T4 were prepared at a concentration of 5 μg/mL in methanol containing 0.1 M ammonium hydroxide and stored at −80° C.

The IS working solution was prepared by mixing and diluting the IS stock solutions to a concentration of 100 ng/L for each compound in methanol containing 50 g/L of each of citric acid, L-ascorbic acid, and DL-dithiothreitol. The IS working solution was stored away from light at −20° C.

The derivatization reagent (SPTPP) was dissolved in DMSO to a concentration of 30 mM.

The derivatization buffer was 0.1 M PBS (pH 8.0).

The termination solution was 1 M NaOH solution.

The acidifier was 5 M HCl solution.

2. Serum Pretreatment (1) Extraction of free THs and related metabolites: A 280 μL sample of human serum was filtered through a Centrifree YM-30 ultrafiltration device (30 kDa molecular weight cutoff, Millipore, Bedford, Mass.) with centrifugation at 1,800×g for 1 h at 37° C. in a Z36HK Hermle centrifuge (Wehingen, Germany). Then, 100 μL of the ultrafiltrate was transferred to a 2 mL glass vial and spiked with 50 μL of 100 ng/L IS working solution.

(2) Derivatization: 30 μL of 0.1 M PBS (pH 8.0) and 20 μL of SPTPP solution in DMSO were added to the sample. After vortex mixing, the mixed solution was heated at 40° C. for 20 min, and 600 μL of 1 M NaOH solution was then added to the reaction mixture. The reaction mixture was extracted twice with 800 μL of ethyl acetate. After purification, 200 μL of 5 M HCl was added to the purified reaction mixture. The acidified purified reaction mixture was extracted twice with 800 μL of ethyl acetate, and the extracts were transferred to a new 2 mL glass vial. All of the purification and extraction steps were performed over ice. Next, the extracts were dried with nitrogen and redissolved in 50 μL of methanol. Finally, the sample containing the SPTPP-derivatized THs was transferred into a glass vial for analysis.

3. UPLC-MS/MS Analysis

The parameters used for UPLC-MS/MS analysis were as follows: UPLC was performed on a Poroshell 120 HPH-C18 column (2.1×100 mm, 2.7 μm, Agilent). The column and sampler temperatures were maintained at 40° C. and 4° C., respectively. The mobile phase, operating at a flow rate of 0.3 mL/min, consisted of methanol as solvent A and Milli-Q water as solvent B. A total of 2-10 μL of each sample was injected onto the column. The gradient elution started at 30% A and was held for 1 min and then increased to 60% A at 15 min, 75% A at 17 min, and 100% A at 18 min. After washing with 100% A for 8 min, the column was re-equilibrated with 30% A for 4 min prior to the next injection. The mass spectrometer was operated in the positive ESI mode with MRM. The conditions for ESI-MS/MS detection were optimized to obtain the highest signal intensity using an optimization program and were as follows: capillary voltage: 3-3.2 KV; desolvation temperature: 500° C.; source temperature: 150° C.; desolvation gas flow rate: 1000 L/h; cone gas flow rate: 150 L/h. The MRM operating conditions are presented in Table 1.

of 5 M HCl was added to each purified reaction mixture. Each acidified purified reaction mixture was extracted twice with 800 μL of ethyl acetate, and the extracts were transferred to new 2 mL glass vials. All of the purification and extraction steps were performed over ice. Next, the extracts were dried with nitrogen and redissolved in 50 μL of methanol. Finally, the samples containing the SPTPP-derivatized THs and related metabolites were transferred into glass vials for UPLC-MS/MS analysis. The concentrations of the calibration standard samples were 0.50 ng/L, 2.00 ng/L, 10.00 ng/L, 40.00 ng/L, 100.00 ng/L, and 300.00 ng/L.

(3) 2 μL of each calibration standard sample was injected into the UPLC-MS/MS system. Calibration curves are constructed by plotting the area ratio of each analyte relative to its IS versus the respective analyte concentrations, and these data are fitted using linear regression. All of the analytes displayed good linearity in the range of 0.5-300 ng/L and the coefficients of determination typically exceeded 0.99. The signal-to-noise (S/N) ratios were used to obtain the limits of detection (LODs) (Table 2).

TABLE 2

Calibration curves and LODs for free THs and related metabolites

| No. | Analyte | Linear equation | Coefficient ($\gamma^2$) | LOD (pg/mL) |
|---|---|---|---|---|
| 1 | MIT | Y = 98.71X − 1.84 | 0.9999 | 0.07 |
| 2 | DIT | Y = 155.24X − 0.09 | 0.9999 | 0.14 |
| 3 | T0 | Y = 74.95X − 0.60 | 0.9999 | 0.09 |
| 4 | T1 | Y = 109.43X − 0.80 | 0.9999 | 0.09 |
| 5 | rT1 | Y = 50.84X − 0.19 | 0.9999 | 0.07 |
| 6 | 3,3'-T2 | Y = 114.33X + 1.49 | 0.9999 | 0.15 |

TABLE 1

MRM operating conditions

| No. | Analyte | RT | Cone voltage (V) | Transition for quantification (m/z) | Collision energy (eV) | Transition (m/z) | Collision energy (eV) |
|---|---|---|---|---|---|---|---|
| 1 | MIT | 8.67 | 88 | 652.04→363.12 | 40 | 652.04→262.16 | 54 |
| 2 | DIT | 10.84 | 44 | 778.88→363.12 | 48 | 778.88→262.16 | 58 |
| 3 | T0 | 10.41 | 80 | 618.17→363.12 | 36 | 618.17→262.16 | 54 |
| 4 | T1 | 13.15 | 36 | 744.07→363.12 | 40 | 744.07→262.16 | 56 |
| 5 | rT1 | 13.73 | 36 | 744.07→363.12 | 40 | 744.07→262.16 | 56 |
| 6 | 3,3'-T2 | 16.04 | 16 | 869.97→363.12 | 48 | 869.97→262.16 | 64 |
| 7 | 3,5-T2 | 14.73 | 16 | 869.97→363.12 | 48 | 869.97→262.16 | 64 |
| 8 | T3 | 16.87 | 52 | 995.80→363.12 | 50 | 995.80→262.16 | 68 |
| 9 | rT3 | 17.22 | 52 | 995.80→363.12 | 50 | 995.80→262.16 | 68 |
| 10 | T4 | 17.52 | 68 | 1121.69→363.12 | 50 | 1121.69→262.16 | 72 |
| 11 | $^{13}C_6$-MIT | 8.67 | 88 | 658.04→363.12 | 40 | 658.04→262.16 | 54 |
| 12 | $^{13}C_6$-3,3'-T2 | 16.04 | 16 | 875.97→363.12 | 48 | 875.97→262.16 | 64 |
| 13 | $^{13}C_6$-T3 | 16.87 | 52 | 1001.80→363.12 | 50 | 1001.80→262.16 | 68 |
| 14 | $^{13}C_6$-T4 | 17.52 | 68 | 1127.69→363.12 | 50 | 1127.69→262.16 | 72 |

4. Calibration Curves and Detection Limits (1) Calibration curves for free THs and related metabolites: The working standard solution was diluted to concentrations of 0.25 ng/L, 1.00 ng/L, 5.00 ng/L, 20 ng/L, 50 ng/L, and 150 ng/L in water and the calibration samples were derivatized with SPTPP.

(2) To obtain the calibration curves, 50 μL of IS working solution, 30 μL of derivatization buffer, and 20 μL of derivatization reagent were added to 100 μL of each working sample of free THs and related metabolites. After vortex mixing, the mixed solutions were heated at 40° C. for 20 min, and then 600 μL of 1 M NaOH solution was added to each sample. Then, each reaction mixture was extracted twice with 800 μL of ethyl acetate. After purification, 200 μL TABLE 2-continued Calibration curves and LODs for free THs and related metabolites

| No. | Analyte | Linear equation | Coefficient ($\gamma^2$) | LOD (pg/mL) |
|---|---|---|---|---|
| 7 | 3,5-T2 | Y = 253.65X − 1.52 | 0.9999 | 0.10 |
| 8 | T3 | Y = 124.37X − 3.05 | 0.9999 | 0.10 |
| 9 | rT3 | Y = 44.09X − 1.92 | 0.9999 | 0.09 |
| 10 | T4 | Y = 129.35X − 0.08 | 0.9999 | 0.03 |

5. Recovery and Repeatability

Recovery experiments were conducted using charcoal-stripped human serum with no detectable levels of any THs. The charcoal-stripped human serum samples were spiked with THs and related metabolites at two levels: 5 ng/L and 50 ng/L. Six replicates were performed. As shown in Table 3, the recoveries of all of the target compounds were in the range of 87.8-116.1%, and the relative standard deviation (RSD) values were less than 12.3%.

TABLE 3

Recoveries and RSD values of THs and related metabolites

| Analyte | Recovery (%) | | % RSD | |
|---|---|---|---|---|
| | 5 ng/L | 50 ng/L | 5 ng/L | 50 ng/L |
| MIT | 92.8 | 108.3 | 5.6 | 4.5 |
| DIT | 105.4 | 106.0 | 8.4 | 3.8 |
| T0 | 102.7 | 103.9 | 3.8 | 4.4 |
| T1 | 116.1 | 104.3 | 2.0 | 3.6 |
| rT1 | 109.7 | 93.0 | 1.7 | 3.2 |
| 3,3'-T2 | 107.9 | 97.6 | 4.5 | 2.0 |
| 3,5-T2 | 100.9 | 96.7 | 9.4 | 2.1 |
| T3 | 106.9 | 95.8 | 7.3 | 2.2 |
| rT3 | 99.9 | 87.8 | 12.3 | 2.1 |
| T4 | 93.9 | 98.9 | 6.6 | 2.8 |

6. Sample Analysis

The samples were analyzed using UPLC-MS/MS. The analytes were identified based on comparison of the retention time and the ratio of the two selected MRM ion transitions with those of standards. The amount of each analyte in a serum sample was then interpolated using the corresponding calibration curve.

Example 2. Analysis of Total THs and Related Metabolites in Serum

1. Instruments and Reagents

Same as described in example 1.

2. Serum Pretreatment (1) Extraction of total THs and related metabolites: A 10 μL sample of human serum spiked with 50 μL of freshly prepared IS working solution dissolved in methanol was added to a glass centrifuge tube. The mixture was kept on ice for 15 min to deproteinate the sample and ensure the release of protein-bound THs. The sample was then centrifuged at 3,500×g for 5 min. The supernatant was transferred to a 2 mL glass vial and the precipitates in the tube were extracted twice with 45 μL of methanol. The supernatant and extracts were combined for SPTPP derivatization.

(2) Derivatization:

Same as described in example 1.

3. UPLC-MS/MS Analysis

Same as described in example 1.

4. Calibration Curves and Detection Limits (1) Calibration curves for total THs and related metabolites: The working standard solution was diluted to concentrations of 0.01 ng/mL, 0.1 ng/mL, 0.5 ng/mL, 2.5 ng/mL, 5 ng/mL, 25 ng/mL, and 150 ng/mL in water and the calibration samples were derivatized with SPTPP.

(2) 50 μL of IS working solution, 30 μL of derivatization buffer, and 20 μL of derivatization reagent were added to 100 μL of each calibration sample. After vortex mixing, the mixed solutions were heated at 40° C. for 20 min, and then 600 μL of 1 M NaOH solution was added to each sample. Then, each reaction mixture was extracted twice with 800 μL of ethyl acetate. After purification, 200 μL of 5 M HCl was added to each purified reaction mixture. Each acidified purified reaction mixture was extracted twice with 800 μL of ethyl acetate, and the extracts were transferred to new 2 mL glass vials. All of the purification and extraction steps were performed over ice. Next, the extracts were dried with nitrogen and redissolved in 50 μL of methanol. Finally, the SPTPP-derivatized calibration samples were transferred into glass vials for UPLC-MS/MS analysis. The concentrations of the calibration samples were 0.01 ng/mL, 0.1 ng/mL, 0.5 ng/mL, 2.5 ng/mL, 5 ng/mL, 25 ng/mL, and 150 ng/mL.

(3) 2 μL of each calibration standard sample was injected into the UPLC-MS/MS system. Calibration curves are constructed by plotting the area ratio of each analyte relative to its IS versus the respective analyte concentrations, and these data are fitted using linear regression. All of the analytes displayed good linearity in the range of 0.01-150 ng/mL and the coefficients of determination typically exceeded 0.99. The S/N ratios were used to obtain the LODs (Table 4).

TABLE 4

Calibration curves and LODs for total THs and related metabolites

| No. | Analyte | Linear equation | Coefficient ($\gamma^2$) | LOD (pg/mL) |
|---|---|---|---|---|
| 1 | MIT | Y = 96.01X + 5.29 | 0.9999 | 0.07 |
| 2 | DIT | Y = 153.86X + 12.35 | 0.9997 | 0.14 |
| 3 | T0 | Y = 73.50X + 2.85 | 0.9999 | 0.09 |
| 4 | T1 | Y = 107.79X + 8.77 | 0.9999 | 0.09 |
| 5 | rT1 | Y = 51.31X + 10.95 | 0.9997 | 0.07 |
| 6 | 3,3'-T2 | Y = 115.57X + 10.35 | 0.9998 | 0.15 |
| 7 | 3,5-T2 | Y = 214.28X + 32.39 | 0.9994 | 0.10 |
| 8 | T3 | Y = 98.06X + 53.59 | 0.9979 | 0.10 |
| 9 | rT3 | Y = 45.45X + 3.89 | 0.9998 | 0.09 |
| 10 | T4 | Y = 124.60X + 15.26 | 0.9997 | 0.03 |

5. Recovery and Repeatability

Recovery experiments were conducted using charcoal-stripped human serum with no detectable levels of any THs. The charcoal-stripped human serum samples were spiked with THs and related metabolites at two levels: 10 ng/L and 100 ng/L. Six replicates were performed. As shown in Table 5, the recoveries of all of the target compounds were in the range of 85.8-112.4%, and the RSD values were less than 12.1%.

TABLE 5

Recoveries and RSD values of THs and related metabolites

| Analyte | Recovery (%) | | % RSD | |
|---|---|---|---|---|
| | 10 ng/L | 100 ng/L | 10 ng/L | 100 ng/L |
| MIT | 85.8 | 94.8 | 12.1 | 2.7 |
| DIT | 96.2 | 86.3 | 8.4 | 1.5 |
| T0 | 94.9 | 104.8 | 4.8 | 2.5 |
| T1 | 93.6 | 95.5 | 7.8 | 2.5 |
| rT1 | 95.2 | 112.4 | 7.2 | 2.7 |
| 3,3'-T2 | 83.7 | 93.1 | 9.8 | 2.6 |
| 3,5-T2 | 102.1 | 99.7 | 7.8 | 3.5 |
| T3 | 91.1 | 89.3 | 10.3 | 4.8 |
| rT3 | 92.3 | 88.5 | 9.4 | 2.1 |
| T4 | 91.4 | 103.5 | 8.5 | 8.4 |

6. Sample Analysis

The samples were analyzed using UPLC-MS/MS. The analytes were identified based on comparison of the retention time and the ratio of the two selected MRM ion transitions with those of standards. The amount of each analyte in a serum sample was then interpolated using the corresponding calibration curve.

These examples describe the exemplified embodiment of this invention. However, the scope of the invention is not limited to these two examples. The invention is amenable to any modifications, alterations, or substitutes of the embodiment without departing from the spirit and scope of the invention. The appended claim is intended to cover such modifications, alterations, or substitutes.

What is claimed is:

1. A method for the simultaneous analysis of thyroid hormones (THs) and related metabolites in serum, comprising:
   1) extracting THs and related metabolites from a serum to be analyzed;
   2) derivatizing extracted THs and related metabolites with (5-N-succinimidoxy-5-oxopentyl)triphenylphosphonium bromide (SPTPP); and
   3) analyzing SPTPP derivatives using ultra-high-performance liquid chromatography-tandem mass spectrometry (UPLC-MS/MS) to accomplish analysis of THs and related metabolites in the serum.

2. The method according to claim 1, wherein the THs and related metabolites include free THs and related metabolites (MIT, DIT, T0, T1, rT1, 3,3'-T2, 3,5-T2, T3, rT3, or T4), and total THs and related metabolites (MIT, DIT, T0, T1, rT1, 3,3'-T2, 3,5-T2, T3, rT3, or T4).

3. The method according to claim 1, wherein the free THs and related metabolites are extracted by the following steps:
   centrifuging the serum using an ultrafiltration device;
   filtering a 200-500 μL sample of the serum using the ultrafiltration device with centrifugation at 37° C. for 0.5-1 h;
   collecting 100-250 μL of the ultrafiltrate; and
   spiking the ultrafiltrate with 50 μL of internal standard (IS) working solution.

4. The method according to claim 1, wherein the total THs and related metabolites are extracted by the following steps:
   adding 10-50 μL of a human serum sample spiked with 50 μL of freshly prepared IS working solution to a glass centrifuge tube;
   keeping the mixture below 0° C. for 15-30 min to ensure the release of protein-bound THs;
   centrifuging the sample at 3,500-12,000×g for 5-20 min;
   collecting the supernatant in a new glass vial;
   extracting an extract from the precipitate in the tube twice with 45 μL of methanol; and
   combining the supernatant and the extract.

5. The method according to claim 3, wherein the IS working solution comprises a mixture of $^{13}C_6$-MIT, $^{13}C_6$-T3, and $^{13}C_6$-T4 (100 ng/L for each compound) and citric acid, L-ascorbic acid, and DL-dithiothreitol (50 g/L for each compound) dissolved in methanol.

6. The method according to claim 1, wherein the step of derivatizing extracted THs and related metabolites with SPTPP includes the following steps: adding 30 μL of a derivatization buffer and 20 μL of derivatization reagent to the extracts of free or total THs and related metabolites; after vortex mixing, heating the mixed solution at 40° C. for 20 min; and adding 600 μL of a termination solution to the reaction mixture.

7. The method according to claim 6, wherein the derivatization buffer is 0.1 M pH 8.0 phosphate-buffered saline, wherein the derivatization reagent is SPTPP dissolved in DMSO to a concentration of 30 mM, wherein the termination solution is 1 M NaOH solution.

8. The method according to claim 1, further comprising:
   prior to UPLC-MS/MS analysis, purifying the reaction mixture using ethyl acetate after the addition of the termination solution;
   adding an acidifier to the purified reaction mixture;
   extracting the SPTPP derivatives using ethyl acetate from the purified reaction mixture; and
   drying the extracts with nitrogen and redissolved in methanol for UPLC-MS/MS analysis.

9. The method according to claim 8, wherein 800 μL of ethyl acetate is used to purify the reaction mixture one to three times after the addition of the termination solution, wherein the acidifier is 5 M HCl solution, wherein the acidified purified reaction mixture is extracted twice with 800 μL of ethyl acetate, and the extracts are transferred to a new 2 mL glass vial, wherein the purification and extraction steps are performed over ice, wherein the extracts are dried with nitrogen and redissolved in 50 μL of methanol, wherein the samples are transferred into glass vials for UPLC-MS/MS analysis.

10. The method according to claim 1, wherein the step of analyzing SPTPP derivatives using UPLC-MS/MS comprises the steps of:
    preparing calibration standards containing THs and related metabolites in water as dilution series;
    derivatizing calibration standards and serum samples with SPTPP;
    analyzing the serum samples using UPLC-MS/MS;
    constructing calibration curves by plotting the area ratio of each analyte relative to its IS versus the respective analyte concentrations, which is fitted using linear regression; and
    interpolating amount of each TH and related metabolite in a serum sample using this linear function.

11. The method according to claim 10, wherein the calibration curves for the THs and related metabolites with different concentration gradients are obtained using the following steps:
    preparing standard stock solutions of THs and related metabolites individually at a concentration of 100 μg/mL in methanol containing 0.1 M ammonium hydroxide and stored at −80° C.;
    preparing a working standard solution by mixing and diluting each standard stock solution to a concentration of 1 μg/mL in methanol;
    preparing calibration curves for free THs and related metabolites by diluting the working standard solution to concentrations of 0.25 ng/L, 1.00 ng/L, 5.00 ng/L, 20 ng/L, 50 ng/L, and 150 ng/L in water and derivatizing the calibration samples with SPTPP; and
    preparing calibration curves for total THs and related metabolites by diluting the working standard solution to concentrations of 0.01 ng/mL, 0.1 ng/mL, 0.5 ng/mL, 2.5 ng/mL, 5 ng/mL, 25 ng/mL, and 150 ng/mL in water and derivatizing the calibration samples with SPTPP.

12. The method according to claim 10, wherein methanol and Milli-Q water are used as mobile phases.

13. The method according to claim 10, wherein UPLC is performed using an Agilent Poroshell 120 HPH-C18 column.

14. The method according to claim 10, wherein UPLC-MS/MS analysis is performed using electrospray ionization.

15. The method according to claim 14, wherein electrospray ionization is performed in the positive mode.

16. The method according to claim 15, wherein the mass spectrometer is operated in the multiple reaction monitoring mode.

17. A kit for the determination of THs and related metabolites in serum, comprising:
    1) a reagents and materials for extracting THs and related metabolites from serum;
    2) an IS working solution containing a mixture of $^{13}C_6$-MIT, $^{13}C_6$-T3, and $^{13}C_6$-T4 (100 ng/L for each compound) and citric acid, L-ascorbic acid, and DL-dithiothreitol (50 g/L for each compound) dissolved in methanol;
3) a standard solution of THs and related metabolites;
4) a derivatization reagent;
5) a derivatization buffer;
6) a termination solution; and
7) an acidifier.

18. The kit according to claim 17, further comprising:
a chromatography column; and
a quality control specimen.

* * * * *